United States Patent [19]
Fuller et al.

[11] Patent Number: 5,500,339
[45] Date of Patent: Mar. 19, 1996

[54] DNA DENATURATION METHOD

[75] Inventors: Carl W. Fuller, Cleveland Heights; Denise A. Pisa-Williamson, Aurora, both of Ohio

[73] Assignee: Amersham Life Science, Inc., Cleveland, Ohio

[21] Appl. No.: 40,304

[22] Filed: Mar. 30, 1993

[51] Int. Cl.$^6$ .................................................. C12Q 1/68
[52] U.S. Cl. ................................................................ 435/6
[58] Field of Search ..................................................... 435/6

[56] References Cited

U.S. PATENT DOCUMENTS

| | | | |
|---|---|---|---|
| 4,795,699 | 1/1989 | Tabor et al. | 435/5 |
| 4,868,115 | 9/1989 | Obayashi et al. | 435/188 |
| 4,962,020 | 10/1990 | Tabor et al. | 435/6 |

OTHER PUBLICATIONS

Oro et al, Influence of the Electrical Permittivity and Counter Ions Content of the Media on the Thermal Denaturation of DNA. Studia Biophysica (1987) 120:51–57.

Norden, B., et al. Structure of Strand Separated DNA in Different Environments Studied by Linear Dichroism, Biopolymeus (1979) 18:2323–2340 (Abstract).

Andersen et al., "A Fast and Simple Technique for Sequencing Plasmid DNA with Sequenase® Using Heat Denaturation," 13(5) *BioTechniques* 678, 1992.

Wallace et al., "A Set of Synthetic Oligodeoxyribonucleotide Primers for DNA Sequencing in the Plasmid Vector pBR322," 16 *Gene* 21, 1981.

Smith et al., "Sequence of the Gene for Iso–1–Cytochrome c in *Saccharomyces cerevisiae*," 16 *Cell* 753, 1979.

Bastia et al., "The Nucleotide Sequence Surrounding the Replication Terminus of R6K," 78 *Proc. Natl. Acad. Sci. USA* 2095, 1981.

Shon et al., "The Nucleotide Sequence of the Replication Origin β of the Plasmid R6K," 257 *J. Biol. Chem.* 13823, 1982.

Straus and Zagursky, "In Vitro Production of Large Single-Stranded Templates for DNA Sequencing," 10(3) *BioTechniques* 376, 1991.

Mead and Kemper, "Chimeric Single–Stranded DNA Phage–Plasmid Cloning Vectors," *Vectors: A Survey of Molecular Cloning Vectors and Their Uses*, Butterworth Publishers, Massachusetts, USA (1986).

Haltiner et al., "A Novel Strategy for Constructing Clustered Point Mutations," 13(3) *Nucleic Acids Research* 1015, 1985.

Chen and Seeburg, "Supercoil Sequencing: A Fast and Simple Method for Sequencing Plasmid DNA," 4(2) *DNA* 165, 1985.

Lim and Pene, "Optimal Conditions for Supercoil DNA Sequencing with the *Escherichia coli* DNA Polymerase I Large Fragment," 5 *Gene Anal. Techniques* 32, 1988.

Hsiao, "A Fast and Simple Procedure for Sequencing Double–Stranded DNA with Sequenase," 19(10) *Nucleic Acids Research* 2787, 1991.

Hattori and Sakaki, "Dideoxy Sequencing Method Using Denatured Plasmid Template", 152 *Anal. Biochem.* 232–238 1986.

*Primary Examiner*—W. Gary Jones
*Assistant Examiner*—David Schreiber
*Attorney, Agent, or Firm*—Lyon & Lyon

[57] ABSTRACT

Method for determining the nucleotide base sequence of a double-stranded closed circular DNA. The method includes heating a solution which includes the DNA in the presence of at least 20% glycerol and/or ethylene glycol to at least 80° C. to provide denatured DNA, and then sequencing the denatured DNA.

5 Claims, No Drawings

DNA DENATURATION METHOD

BACKGROUND OF THE INVENTION

This invention concerns methods for denaturing double-stranded plasmid DNAs.

It is common in the art to determine the nucleotide base sequence of DNA molecules. One type of DNA molecule used in such procedures is supercoiled plasmid DNA. Such DNA must be denatured in some manner prior to use in a chain-termination sequencing reaction. Generally, the DNA is denatured by treating with 0.2M NaOH, and then ethanol precipitating the denatured strands so that they may be used in a sequencing protocol. Denaturation by simple heating is not generally possible since the melting temperature of covalently closed circular DNAs is above the boiling point (100° C., see below). Common protocols are described by Tabor and Richardson, U.S. Pat. Nos. 4,795,699 and 4,962,020.

SUMMARY OF THE INVENTION

Applicant has determined that non-caustic agents, compatible with enzymes used for performing sequencing procedures, can be used to enhance denaturation of supercoiled double-stranded plasmid DNA. These agents include glycerol and ethylene glycol which lower the melting temperature of DNA. For example, a 1% solution of glycerol will lower the melting temperature (Tm) of DNA by about 0.4° C. Ethylene glycol lowers melting temperature a similar amount. Thus, the melting temperature of most DNAs in 70% glycerol is about 45° C. (or lower if such DNA contains deazaguanine or deoxyinosine in place of deoxyguanine, or if α-thio nucleotides are substituted for standard oxygen-containing nucleotides). Thus, glycerol or ethylene glycol can be used to allow ready denaturation (at low temperature) of double-stranded plasmid DNAs, and sequencing reactions can be performed with such denatured solutions without further manipulation of the solution. The products of the sequencing reactions can then be run in electrophoretic gels of the type described by Fuller in "Electrophoresis of Nucleic Acid Fragments", U.S. Ser. No. 07/928,852, filed Aug. 10, 1992, hereby incorporated by reference herein.

Thus, in a first aspect, the invention features a method for determining the nucleotide base sequence of a double-stranded closed circular (e.g., supercoiled) plasmid DNA. The method includes treating a solution which includes the DNA in the presence of at least 20% (v/v) glycerol and/or 20% (v/v) ethylene glycol by heating to a temperature of at least 80° C. to provide denatured DNA. When circular DNA is denatured, the denatured strands remain tightly wrapped around each other and the strands are no longer stiff like double-stranded molecules. DNA denatured in this way sediments much faster than other forms (single-stranded, double-stranded or supercoiled), suggesting that the molecules collapse into a tightly interwound ball of DNA This has been called form IV DNA. This denatured DNA can then be sequenced using a method described by Tabor and Richardson, supra (hereby incorporated by reference herein), or its equivalent. As noted above, the products of a sequencing reaction can then be run in a glycerol tolerant gel as described by Fuller, supra.

In preferred embodiments, between 30% and 50% glycerol or ethylene glycol is used in the procedure, and the DNA is heated to between 80° C. and 100° C.

This invention provides a superior method for denaturing DNA in that supercoiled plasmid DNA which has a melting temperature above 100° C. can be readily denatured by heating at 90° C. This allows avoidance of the cumbersome step of addition of alkali, followed by ethanol precipitation, to allow subsequent sequence analysis. The method is also superior to simple boiling of the DNA where only a fraction of DNA actually is denatured. (See, Andersen et al., 13 *BioTechniques* 678, 1992.) With glycerol or ethylene glycol, denaturation is much more efficient and thus allows much less DNA to be used in a sequencing reaction.

By "supercoiled plasmid DNA" is meant any double-stranded circular DNA with continuous, unbroken strands. This DNA can be bacterial plasmids, phage (in packaged or replicative form) or constructed in vitro. The length of time the DNA remains denatured depends on conditions. While re-naturation is favored thermodynamically, it is kinetically hindered because of the intertwisting of the strands. Many relatively stable "false starts" will occur before the correct bases in the two strands can find each other. Applicant believes that re-naturation even under "ideal" conditions requires hours to days.

In a related aspect, the invention features a kit for DNA sequencing, having in separate containers: a DNA polymerase, a pure solution of glycerol and/or ethylene glycol in a concentration at least 40% (v/v), and at least one chain terminating agent (e.g., a dideoxynucleotide). Preferably, a pure solution of about 40% of each of ethylene glycol and glycerol is provided (e.g., as an aqueous solution free of any protein or other enzymatic agent).

Other features and advantages of the invention will be apparent from the following description of the preferred embodiments thereof, and from the claims.

DESCRIPTION OF THE PREFERRED EMBODIMENTS

Alkali/Heating Methods

Until about 1986, dideoxy-DNA sequencing was largely limited to single-stranded template DNAs. Hence, the popularity of single-stranded vectors such as M13mp8, M13mp9, M13mp12, M13mp13, M13mp18, M13mp19, mWB2348, mWB3295 and mWB3225. Methods were also developed for converting double-stranded DNA into single-stranded DNA using restriction endonucleases and denaturation of the DNA by heating (for example, Wallace et al., "A Set of Synthetic Oligonucleotide Primers for DNA Sequencing in the Plasmid Vector pBR322", 16 *Gene* 21, 1981, and Smith et al., "Sequence of the Gene for Iso-1-Cytochrome C in Saccharomyces cerevisiae", 16 *Cell* 753 1979) Others used a combination of restriction endonucleases and exonucleases to create single-stranded templates (Bastia et al., "The Nucleotide Sequence Surrounding the Replication Terminus of R6K", 78 *Proc. Natl. Acad. Sci. USA* 2095, 1981; Shon et al., "The Nucleotide Sequence of the Replication Origin β of the Plasmid R6K", 257 *J. Biol. Chem.* 13823, 1982; Straus and Zagursky, "In Vitro Production of Large Single-Stranded Templates for DNA Sequencing", 10 *BioTechniques* 376, 1991). These methods did not become popular or widely-used because the manipulations of the DNA were time-consuming and the results were variable. New sequencing vectors with which one could isolate either single- or double-stranded DNA were also introduced (Mead and Kemper, in "Vectors: A Survey of Molecular Cloning Vectors and Their Uses", Butterworth Publishers, Massachusetts, USA (1986)).

In 1985, a new method for sequencing plasmid DNAs was discovered (Haltiner et al., 13 *Nucleic Acids Research* 1015, 1985; Chen and Seeburg, "Supercoil Sequencing: A Fast and Simple Method for Sequencing Plasmid DNA:, 4 DNA 165, 1985; Hattori and Sakaki, "Dideoxy Sequencing Method Using Denatured Plasmid Templates", 152 *Anal. Biochem.* 232, 1986; Lim and Pene, "Optimal Conditions for Supercoil DNA Sequencing with the *E. coli* DNA Polymerase I Large Fragment", 5 *Gene Anal Techniques* 32, 1988). The plasmid DNA is denatured using dilute NaOH. The DNA is usually precipitated with ethanol following denaturation (to ensure sufficient concentration) and then sequenced as if it were single-stranded. As discussed below, the use of alkali is required because plasmid DNAs do not denature readily in neutral solution. The two strands of the denatured DNA remain intertwined because the hundreds of helical turns present in the native structure are still present in the denatured molecules. The strands renature only slowly because of this inter-twining of the strands.

Plasmid DNAs, when denatured using this method give sequences that are of high quality, although they never match the quality of sequences obtained using single-stranded DNA (see, Fuller, U.S. Ser. No. 07/927,562, filed Aug. 6, 1992, hereby incorporated by reference herein). Nevertheless, plasmid templates represent the majority of DNAs sequenced currently.

When sequencing single-stranded DNA, one merely mixes the isolated DNA with primer and a suitable buffer. This mixture is heated briefly to 37°–65° C. and cooled to ensure efficient annealing of the primer to the template. The entire process takes 10–30 minutes at most. When sequencing a plasmid by alkaline denaturation, one mixes the DNA with 0.1 volumes of 2.0M NaOH and incubates at 20°–37° C. for 5–30 minutes. Then a volume of concentrated buffer with a pH of 4.5–7.5 is added to neutralize the NaOH and 2–3 volumes of ethanol are added to precipitate the DNA. Precipitation is completed at −80° C., −20° C., or up to +20° C. in a period of 15 minutes–18 hours. The DNA is pelleted in a centrifuge 20–30 minutes at 4°–20° C. The pellet is washed with 70% ethanol and again centrifuged for 5–10 minutes. The pelleted DNA is then air-dried or vacuum-dried 5–30 minutes. Finally, the DNAs are mixed with primer and buffer and annealed in a manner that is essentially identical to that for single-stranded DNA. Thus, the preparation of a typical number of samples for sequencing (12 plasmids) will take a minimum of 2–3 hours and often takes much longer. A procedure which avoids the precipitation step has also been published (Hsiao, 19 *Nucleic Acids Research* 2787, 1991). This method is considerably faster but requires that the DNA be prepared at a fairly high concentration—and this is typically achieved by precipitation with ethanol resulting in relatively little overall improvement. It also will not generally work for any sequencing method which is sensitive to salt concentrations of about 50 mM or higher.

Use of Glycerol/Ethylene Glycol

The thermal denaturation of plasmid DNA samples was measured using a Gilson Response spectrophotometer equipped with a scanning temperature controller. Absorbance at 260 nm of a solution of pUC19 DNA (50 μg/ml) was recorded as a function of increasing temperature from 20°–100° C. Two thermal transitions were observed for each sample, a minor one representing the small amount of nicked and linear plasmid present in the sample, and a major one resulting from denaturation of the covalently closed circular DNA. The melting temperatures were determined from a first-derivative graph of the data. The solvent was 40 mM Tris.HCl, pH 7.5, 20 mM $MgCl_2$, 50 mM NaCl (the annealing and reaction buffer for sequencing with T7 DNA polymerase), and the indicated concentration of glycerol. Only part of the thermal transition for closed circular DNA was observable for the case of no added glycerol.

The data show that the melting temperature of a typical plasmid DNA in sequencing buffer is somewhat higher than 100° C. Thus, the DNA cannot be denatured by heating with ordinary laboratory equipment. The addition of glycerol and/or ethylene glycol decreases the melting temperature of the DNA. Each 10% increment in glycerol concentration results in a 4° C. decrease in melting temperature. Furthermore, glycerol, unlike many other materials, does not interfere with DNA sequencing reactions even at a concentration as high as 40%.

It is also well known that the presence of salts (in this case specifically NaCl and $MgCl_2$) will increase the melting temperature of DNA. These can be avoided in the present method during the denaturation of the DNA at high temperature. DNA is also prone to hydrolysis at high temperature in the presence of $Mg^{2+}$. Thus, omission of $MgCl_2$ from the denaturation step helps to preserve the DNA.

The following experiments were performed to demonstrate utility of the invention. Those in the art will recognize that various amounts of glycerol or ethylene glycol, or mixtures thereof (e.g., 20% +20%), can be used within the scope of the invention. Thus, these examples are not limiting in the invention.

In one experiment, a mixture of 3 μg of plasmid DNA (pUC19) and 0.5 pmol of "−40" sequencing primer was incubated at 100° C. (boiling water bath) for 5 minutes (to denature) followed by chilling on ice 5 minutes and incubating at 37° C. for 10 minutes (to anneal). Some of the samples contained glycerol and/or sequencing reaction buffer (0.2M Tris.HCl pH 7.5, 0.1M $MgCl_2$, 0.25M NaCl) in addition. Following the annealing, the primer-template mixture was used for sequencing exactly as recommended for single-stranded M13 DNA sequencing with the SEQUENASE® Version 2.0 DNA sequencing kit (adding buffer as required, United States Biochemical Corporation, Cleveland, Ohio).

Specifically, pUC19 DNA was sequenced following alkaline denaturation, heat denatured pUC19 DNA prepared in the presence of reaction buffer and 0%, 25%, 40% or 50% glycerol. This DNA was sequenced. Heat denatured pUC19 DNA prepared without reaction buffer but containing 0%, 25%, 40% or 50% glycerol was also used and then sequenced. For denaturations which contained buffer, 50% glycerol gave a sequence with similar intensity (especially close to the primer) to that of alkali-denatured DNA. For the case of denaturation in the absence of buffer, 40% glycerol was sufficient to provide good sequencing data.

In another experiment, alkaline denaturation was compared with glycerol denaturation for two additional plasmids each primed with two different primers. The heat-denatured samples had 40% glycerol and no buffer present during denaturation. In each case, the sequence obtained by heat denaturation in the presence of glycerol was considerably darker than that obtained by alkaline denaturation, indicating more efficient denaturation and priming using this method.

EXAMPLE 1

The following is a detailed method of those experiments discussed above.

Three μg of plasmid DNA was dissolved in 10 μl of TE (Tris 10 mM, EDTA 1 mM, pH 7.5) buffer. 8 μl glycerol and 1 µl of primer (0.5 pmol/µl) was added. The mixture was heated to 100° C. in a capped vial for 5 minutes, chilled briefly on ice, and centrifuged briefly to collect the liquid at the bottom of the tube. 2 µl SEQUENASE® Reaction Buffer (0.2M Tris.HCl pH 7.5, 0.1M $MgCl_2$, 0.25M NaCl) was added. The tube was incubated at 37° C. for 10–15 minutes to allow annealing. 2 µl of diluted labeling mix (SEQUENASE® Kit), 1 µl of 0.1M DTT and 2 µl of SEQUENASE® T7 DNA polymerase was added. This labeling mix was incubated for 5 minutes at room temperature (about 20° C., or up to 37° C.). This mixture was divided into 4 termination reactions containing termination mixes from the SEQUENASE® Kit. The termination reactions were incubated for 5 minutes at 37°–50° C. 4 µl of Stop Solution was added and the products run on a glycerol-tolerant DNA sequencing gel (see, Fuller, supra).

Other embodiments are within the following claims.

We claim:

1. Method for determining the nucleotide base sequence of a double-stranded closed circular DNA, consisting essentially of:

heating a solution comprising said DNA in the presence of a total of at least 20% and 50% (v/v) glycerol and/or ethylene glycol to at least 80° C. to provide denatured DNA, wherein said amount of glycerol and/or ethylene glycol is at most 50% (v/v);

reducing the concentration of said glycerol and/or ethylene glycol in contact with said denatured DNA so that said denatured DNA can be sequenced; and sequencing said denatured DNA by a chain termination sequencing method.

2. The method of claim 1, wherein said glycerol is provided in an amount between 30% and 50% (v/v).

3. The method of claim 1, wherein said ethylene glycol is provided in an amount between 30% and 50% (v/v).

4. The method of claim 1, wherein a mixture of glycerol and ethylene glycol is used in said method of sequencing.

5. The method of claim 4, wherein said mixture comprises between 10 and 30% (v/v) glycerol and between 10 and 30% (v/v) ethylene glycol.

* * * * *